United States Patent
Steinmetz

(10) Patent No.: US 8,981,969 B2
(45) Date of Patent: Mar. 17, 2015

(54) ALARM APPARATUS FOR A PILOT'S HEADSET

(71) Applicant: Robert Bosch GmbH, Stuttgart (DE)

(72) Inventor: Martin Steinmetz, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 120 days.

(21) Appl. No.: 13/729,334

(22) Filed: Dec. 28, 2012

(65) Prior Publication Data

US 2013/0169451 A1 Jul. 4, 2013

(30) Foreign Application Priority Data

Dec. 30, 2011 (DE) .......................... 10 2011 090 162

(51) Int. Cl.
| | |
|---|---|
| *G01C 21/00* | (2006.01) |
| *B64D 45/00* | (2006.01) |
| *A61B 5/18* | (2006.01) |
| *H04R 1/10* | (2006.01) |
| *A61B 5/11* | (2006.01) |
| *A61B 5/00* | (2006.01) |

(52) U.S. Cl.
CPC . *B64D 45/00* (2013.01); *A61B 5/18* (2013.01); *H04R 1/10* (2013.01); *A61B 5/746* (2013.01); *A61B 5/747* (2013.01); *A61B 5/11* (2013.01); *A61B 5/6803* (2013.01); *A61B 2562/028* (2013.01)
USPC .......................... 340/974; 340/970; 340/945

(58) Field of Classification Search
USPC ............................ 340/967, 970, 575, 576, 974
See application file for complete search history.

(56) References Cited

U.S. PATENT DOCUMENTS

| | | | | |
|---|---|---|---|---|
| 3,999,177 | A | * 12/1976 | Greene | 340/575 |
| 4,272,764 | A | * 6/1981 | Herr et al. | 340/575 |
| 4,879,542 | A | * 11/1989 | Elsey | 340/326 |
| 5,373,857 | A | 12/1994 | Travers et al. | |
| 5,682,144 | A | * 10/1997 | Mannik | 340/575 |
| 5,684,461 | A | 11/1997 | Jones | |
| 6,067,020 | A | * 5/2000 | Wimmer | 340/575 |
| 8,063,786 | B2 | * 11/2011 | Manotas, Jr. | 340/576 |
| 2003/0061001 | A1 | 3/2003 | Willins et al. | |
| 2009/0203318 | A1 | 8/2009 | Haan | |
| 2010/0002893 | A1 | 1/2010 | Theverapperuma et al. | |
| 2010/0158264 | A1 | 6/2010 | Marten | |
| 2010/0246846 | A1 | 9/2010 | Burge et al. | |
| 2010/0253526 | A1 | * 10/2010 | Szczerba et al. | 340/576 |
| 2011/0001623 | A1 | * 1/2011 | Kim | 340/575 |
| 2011/0121976 | A1 | * 5/2011 | Johns et al. | 340/576 |

FOREIGN PATENT DOCUMENTS

| | | |
|---|---|---|
| DE | 2900968 | 7/1980 |
| GB | 2434017 | 7/2007 |

* cited by examiner

*Primary Examiner* — Kerri McNally
(74) *Attorney, Agent, or Firm* — Michael Best & Friedrich LLP

(57) ABSTRACT

The invention relates to an alarm apparatus (1) for a pilot's headset (3) and to a pilot's headset having such an alarm apparatus. The alarm apparatus comprises an attitude sensor (11), which detects its inclination relative to a starting position or the horizontal, and a measuring device (12) for recording a period for which the inclination recorded by the attitude sensor exceeds a stipulated inclination tolerance limit. In addition, the alarm apparatus has a means (13) which is set up to trigger an alarm signal when a recorded period of the inclination tolerance limit being exceeded is longer than a preset maximum period.

21 Claims, 3 Drawing Sheets

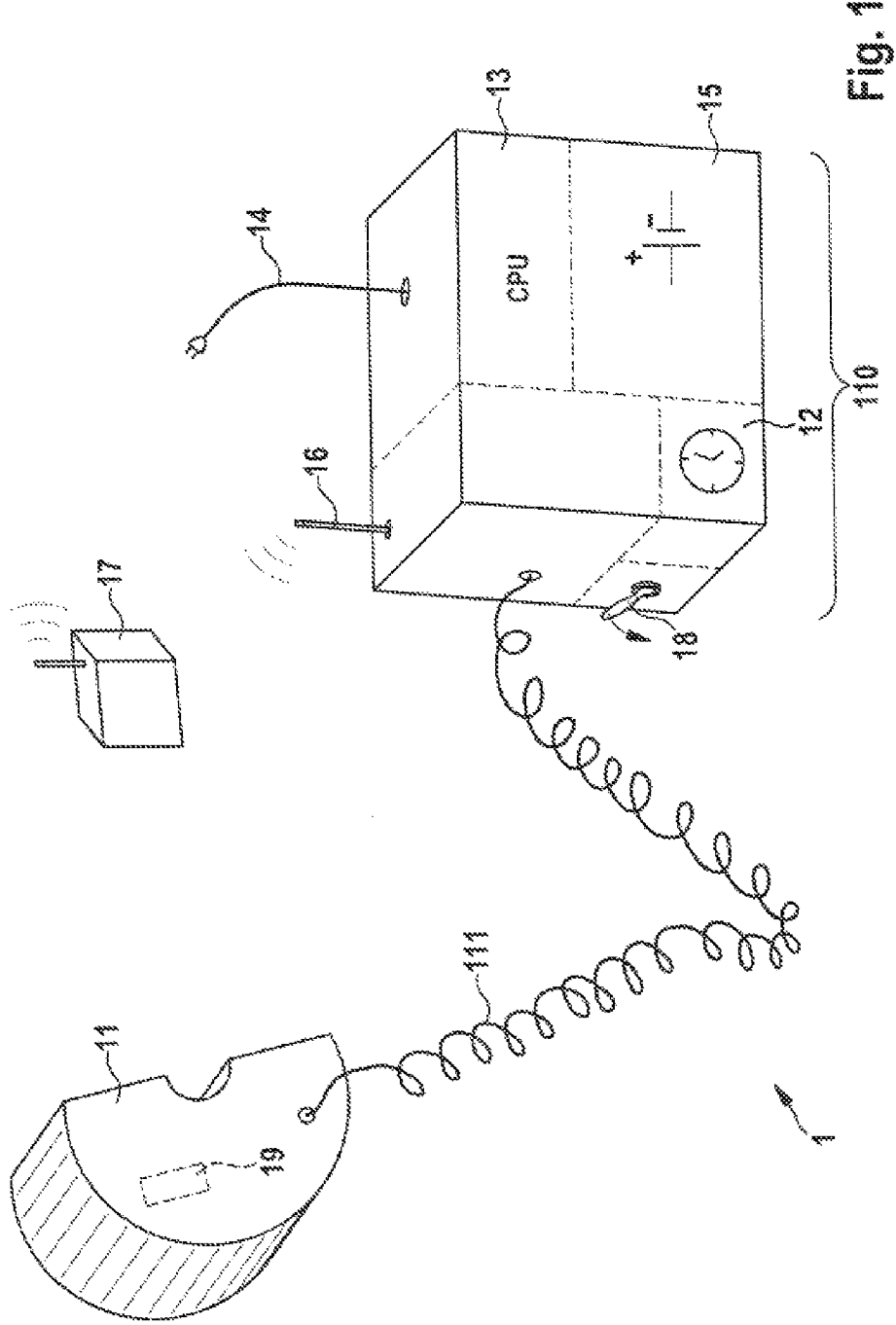

US 8,981,969 B2

ALARM APPARATUS FOR A PILOT'S HEADSET

BACKGROUND OF THE INVENTION

The present invention relates to an alarm apparatus for a pilot's headset and to a pilot's headset having an alarm apparatus. In addition, the invention relates to a method for controlling an alarm apparatus for a pilot's headset.

In airplanes and other aircraft, the respective pilots usually wear what are known as headsets. By way of example, US 2010/0002893 A1 discloses wireless pilot's headsets.

Normally, such headsets comprise two ear cups which are connected to one another by means of a headband. Mounted on one side is a microphone bow which is directed forward in the direction of the mouth of a user.

Firstly, headsets are used for protecting the hearing in loud cockpits; secondly, they are frequently connected to appliances which provide radio contact with one or more base stations or which the occupants can use to communicate with one another.

In the case of longer flights based on visual flight rules (VFR), it is necessary for a pilot to occasionally look at the aviation chart. In doing this, he interrupts observation of the airspace for a few seconds. In particular, this presents the risk of collisions with aircraft which are themselves in instrument flight.

Although collision warning systems are able to react to transponders and/or what are known as FLARM signals and to indicate aircraft close by to the pilot, this requires these other aircraft to be equipped with a transponder and/or an FLARM system. These collision warning systems are also technically complex and costly.

The present invention therefore has the object of providing an apparatus which is simple and inexpensive to implement and which can be used to effectively reduce the risk of collision in air traffic.

SUMMARY OF THE INVENTION

The invention proposes an alarm apparatus, a pilot's headset having an alarm apparatus and a method for controlling an alarm apparatus.

The present invention achieves the aforementioned object by providing means which are used to indirectly check the attention that a pilot is apparently paying to the airspace surrounding him. To this end, an alarm apparatus for a pilot's headset having at least one earphone is provided. The earphone may be a headphone cup or an in-ear earphone, which is introduced into a portion of the auditory canal or which is suspended in the ear cup.

The alarm apparatus according to the invention simply has an attitude sensor which detects its inclination relative to a starting position (for example the horizontal). This starting position corresponds particularly to a reference inclination of the head at which the airspace can be observed by the pilot. Furthermore, the alarm apparatus comprises a measuring device for recording a period for which the inclination recorded by the attitude sensor exceeds an inclination tolerance limit. Finally, the alarm apparatus comprises means which are suitable for triggering an alarm signal when a recorded period of the inclination tolerance limit being exceeded is longer than a preset maximum period.

Said period captured by the measuring device denotes the period of time for which the inclination tolerance limit is exceeded continuously or with interruptions, the duration of which is below a preset minimum time limit. The measurement of the period for which the inclination tolerance limit is exceeded is thus reset when the inclination falls back into the tolerance range for at least one preset minimum time. The minimum time may advantageously be approximately 3 seconds, as a result of which the period for which the inclination tolerance limit is exceeded is reset only when there is a drop below the tolerance limit for at least 3 seconds, since the pilot has then observed the airspace in the direction of flight, or at least has kept his head in an appropriate position, for at least 3 seconds; however, an immediate reset is also possible, corresponding to a minimum time of 0 seconds.

A suitable means that is set up to trigger an alarm signal where necessary is a computation unit (such as a microprocessor) having a connection to a unit for producing an alarm (for example a loudspeaker). The recorded period for which the inclination tolerance limit is exceeded is then transmitted to the computation unit, which compares it with the preset maximum period and if necessary provides the stimulus to produce the alarm signal.

The alarm apparatus is set up to be mounted on or integrated into the pilot's headset. When the headset is worn, the detected inclination of the attitude sensor corresponds to the posture of the pilot's head. The present invention thus allows the pilot to lower his head for a preset maximum period, for example in order to look at an aviation chart, manuals or instruments. Such a head inclination is advantageously outside the inclination tolerance limit that can be assumed for looking out into the airspace. This inclination tolerance limit can also be specified by means of an angle range between the starting position, that is to say the reference inclination, and the inclination tolerance limit and may be preset by the manufacturer or a user. The angle range may also comprise two angles which are specified in different directions relative to a starting position for the sensor and relative to the horizontal. The two arms of the angle range then correspond to the inclination tolerance limit for an inclination in the respective direction, that is to say forward, or down and behind, or upward, the reference inclination then being between the two inclination tolerance limits.

Suitable angle ranges are ±5°, ±10°, ±15°, ±20°. Alternatively, the inclination tolerance limit may correspond to an asymmetric angle range relative to the horizontal, that is to say so that the tolerance range covers a greater inclination upward than downward, for example. The alarm apparatus can thus be matched to individual posture differences. Similarly, this means that a greater angle range may be provided for observing the airspace above the aircraft. Similarly, it is possible to provide a different maximum period for each of the two inclination tolerance limits.

If the inclination exceeds the prescribed tolerance limit for too long, that is to say that the pilot does not observe the airspace in the direction of flight for longer than a preset maximum period, for example, then the alarm device takes effect by triggering an alarm signal which reminds the pilot that he has neglected the airspace surrounding him for too long and that he should pay attention to it again.

As explained above, headsets are usually part of the basic equipment of a pilot. Advantageously, a pilot thus does not need to wear or even attach to himself an additional, possibly disruptive or at least unfamiliar kind of instrument. Instead, he can put on a headset in the usual manner. If said headset is provided with an alarm apparatus according to the invention, the pilot is automatically protected thereby.

The alarm signal may be a conspicuous flashing light in the cockpit, for example. Alternatively, or in addition, an audible alarm signal can be triggered. An alarm apparatus having an adjustable volume allows customization to the individual hearing capabilities or habits of the pilot. This may be provided in the form of a continuous siren sound, multiple successive bleeps and/or an automatic text announcement, for example. Such an audible warning signal can be output via onboard loudspeakers or via the at least one earphone of the headset itself. Ideally, the alarm signal is terminated automatically when the head posture of the pilot is within the tolerance range again for the provided minimum time.

In one advantageous embodiment, the audible warning signal becomes increasingly louder and/or more intensive over time. Alternatively or additionally, the volume of the warning signal may be adjustable. If it is a volume which increases over time, the manufacturer or a user can prescribe the upper limit and/or the lower limit for the volume.

It is advantageous to have an alarm device in which the volume can be varied by the user only within a prescribed range. It is thus possible for the manufacturer to stipulate a certain minimum volume. This is particularly advantageous when the use of the alarm device is a safety requirement.

The alarm signal may have a preset duration, such as 1 second, 2 seconds or 5 seconds. Alternatively, the alarm apparatus may be designed such that the alarm signal stops only when the pilot has raised his head again at least for the period of the minimum time. To this end, the measuring device of the alarm apparatus is preferably set up to also measure a time for which the inclination recorded by the attitude sensor does not exceed the inclination tolerance limit. In use, this period corresponds to the period of time for which it can be assumed, on the basis of the head inclination of the pilot, that the pilot is looking forward again. If this period is longer than a preset minimum period of time, such as 1 second, 2 seconds, 3 seconds or more, the alarm signal is terminated, otherwise it is continued. In this way, the alarm apparatus prompts the pilot particularly urgently to check the airspace. Such an alarm apparatus thus provides the pilot and other aviators with particularly effective protection.

The preset maximum period for which the inclination tolerance limit can be exceeded without an alarm signal being triggered may be a time between 2 and 60 seconds, for example. Advantageously, the maximum period is between 5 and 40 seconds, and ideally a maximum period of no more than 10, 20 or 30 seconds is provided. In one advantageous embodiment of the alarm apparatus, a user can stipulate or change this period himself. This allows customization to current visible conditions, for example. In this case too, it is advantageous for safety reasons if the maximum period can be adjusted only to a limited degree, that is to say that, by way of example, a user cannot adjust it to a time which is longer than 30 seconds, for example.

In one development of the invention, the alarm apparatus according to the invention may be set up to send a distress signal if the inclination tolerance limit is exceeded for too long (e.g. for 120 seconds) without the pilot reacting to the alarm signal. In this case, a medical emergency can be assumed. The distress signal can be sent by means of a mobile telephone connected to the pilot's headset or by means of an onboard radio, for example. In this case, it is advantageous if the alarm apparatus sends an emergency signal, which is different than the alarm signal, to the pilot once again before the distress signal is sent, so that the pilot can avoid a false alarm if there is no emergency.

Preferably, the alarm apparatus is already integrated in the pilot's headset. In one embodiment, the alarm apparatus is at least to some extent incorporated in or mounted on a microphone bow which the pilot's headset likewise comprises. The microphone bow for its part may be mounted on or connected to the at least one earphone. In this case, the pilot's headset may be designed such that the microphone bow can be pivoted such that the at least one earphone is worn either on the left or on the right ear of the pilot and the microphone bow projects in front of the mouth of the pilot in each case. Preferably, the alarm apparatus can then be adjusted to suit the respective position of the microphone bow, for example by a manually operated switch or automatically if the pilot's headset or the alarm apparatus itself additionally comprises a position sensor for the microphone bow. Ideally, the alarm apparatus is to a large extent integrated completely in the pilot's headset, particularly in the earphone(s). Since the microphone bow is directed in front of the mouth of the pilot, the direction of flight can be detected by a simple switch, for example, which is operated automatically by the adjustment of the microphone bow, so that the tolerance limit or the angle range is automatically set correctly in the case of an asymmetric angle range, that is to say in the case of a different tolerance limit for tilting forward and back.

The pilot's headset according to the invention may be set up such that the alarm apparatus it contains switches on automatically when the pilot's headset is put on. This can be detected over a range of basic positions for the pilot's headset, for example. If the pilot's headset comprises a headband, it may also be set up such that a headband tension beyond a minimum value prompts the alarm apparatus to be switched on. Finally, a heat sensor may be provided on the pilot's headset, said heat sensor being suitable for registering use of the pilot's headset and triggering switch-on of the alarm apparatus. Such a pilot's headset is particularly safe because the pilot does not need to think about switching on the alarm apparatus. In addition, misactivations can thus be easily and effectively avoided.

Further advantages and refinements of the invention can be found in the description and the accompanying drawing.

It goes without saying that the features cited above and those that are yet to be explained below can be used not only in the respectively indicated combination but also in other combinations or on their own without departing from the scope of the present invention.

The invention is shown schematically in the drawing with the aid of exemplary embodiments and is described in detail below with reference to the drawing.

BRIEF DESCRIPTION OF THE DRAWINGS

FIG. 1 schematically shows an alarm apparatus for a pilot's headset;

DETAILED DESCRIPTION

Figure 2A:
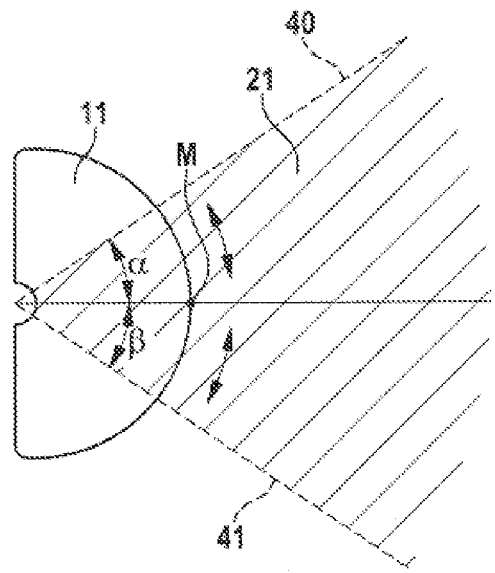
FIG. 2A shows an uninclined attitude sensor and an angle range corresponding to a tolerance inclination limit value.

FIG. 1 schematically shows an alarm apparatus 1 according to the invention. It comprises an attitude sensor 11 which is connected to a unit 110 by means of a cable 111. This unit 110 contains particularly a measuring device 12 for recording a period for which the inclination recorded by the attitude sensor 11 exceeds a stipulated inclination tolerance limit. As has been mentioned above, the inclination tolerance limit may be expressed by virtue of an angle range 21.

In addition, the unit 110 comprises a computation unit 13 and a connection for an onboard radio or an avionics unit for an aircraft. Optionally, an antenna 16 may also be provided which connects the alarm apparatus 1, for example by means of a Bluetooth link, to the onboard radio, the avionics and/or further components—for example a mobile telephone.

Figure 2B:
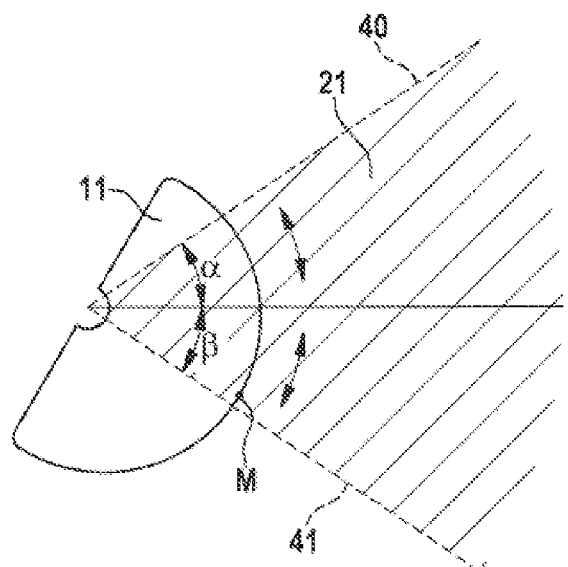
FIG. 2B shows the angle range from FIG. 2A, with the attitude sensor being inclined.

FIGS. 2A and 2B schematically show such an angle range 21, the arms 40, 41 of which indicate the inclination tolerance limit in both directions; for the purpose of better understanding, these figures will be explained first of all at this juncture before further features which are shown in FIG. 1 are described. The angle range 21 shown in FIGS. 2A and 2B comprises the angles α and β, which are shown relative to the horizontal as a reference inclination on both sides. On the attitude sensor 11, which is shown schematically in the side view, a marking point M is shown for the purpose of better explanation. In FIG. 2A, the marking point M is on the horizontal line, and the attitude sensor 11 is therefore not inclined. By contrast, the attitude sensor 11 is inclined relative to the horizontal in FIG. 2B, and the marking point M is situated beneath the horizontal but still in the angle range 21 shown, that is to say still in the inclination tolerance range. This indicates that the inclination shown does not yet exceed the inclination tolerance limit shown by the arm 41. In the event of further inclination to an extent such that the marking point M is situated outside the angle range 21, and is therefore situated beneath the arm 41, the marking point M and hence the inclination would exceed the inclination tolerance limit. The period of the inclination of such severity is recorded by the measuring device 12 and compared with a maximum period. In the event of the maximum period being exceeded, an alarm signal is triggered.

In order to measure the period, the exceeding of the inclination tolerance limit, that is to say the departure from the angle range 21, involves a first timer—not shown for the sake of clarity—in the measuring device 12 being started which is reset only when the inclination is within the angle range 21 again, and hence the marking point is above the arm 41 again, that is to say within the inclination tolerance limit.

In one variation of the invention, a second timer is provided which measures the interval of time that has elapsed since the marking point M reentered the angle range 21. The first timer is reset only when this interval of time has elapsed, and therefore the inclination and hence the marking point M are within the inclination tolerance range determined by the angle range 21 for a predetermined time, particularly a minimum time, for example between 2 and 5 seconds. Accordingly, the triggering of an alarm is also controlled.

Figure 3:
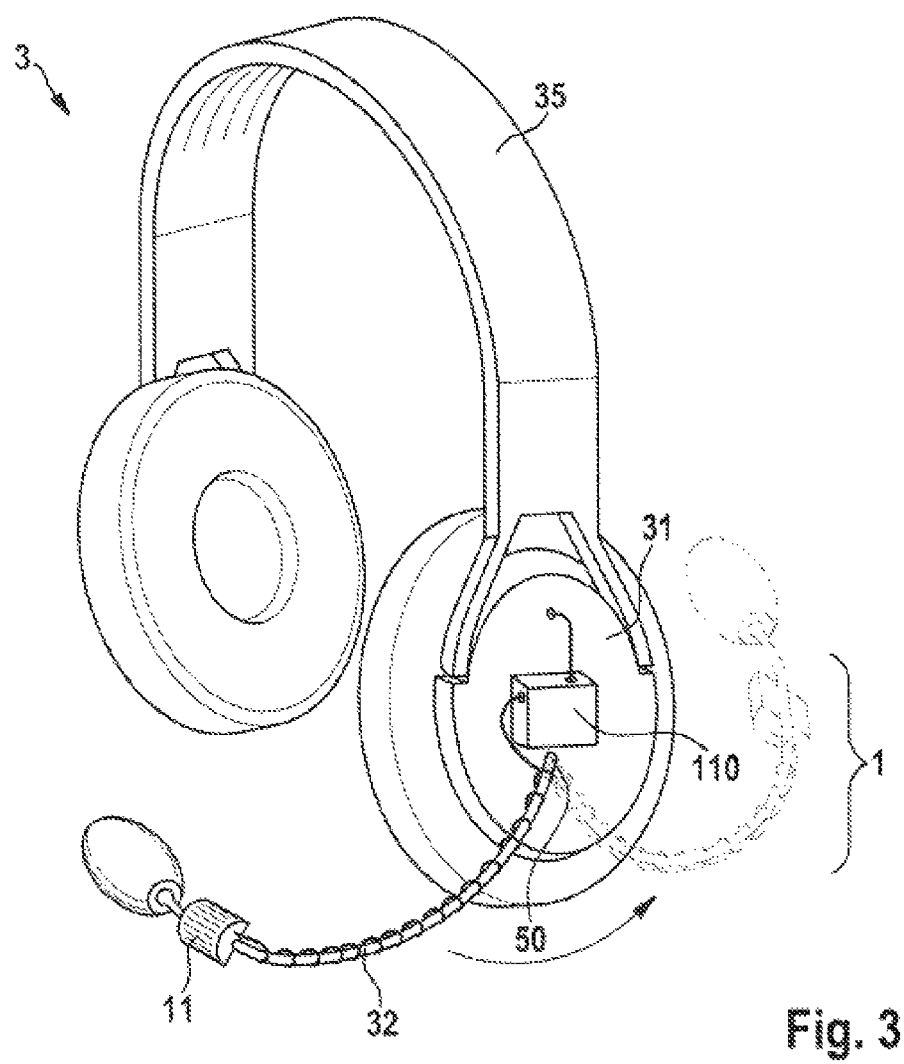
FIG. 3 shows a pilot's headset with an alarm apparatus according to the invention.

FIG. 1 shows a computation unit 13 which is set up to trigger an alarm signal if necessary. A connecting cable 14 can be used to connect the alarm apparatus and particularly the computation unit 13 to a pilot's headset 3 (FIG. 3). When an alarm is triggered, an audible warning tone can be produced in at least one earphone of the pilot's headset 3. When there is drop below the inclination tolerance limit again, that is to say that the marking point M is in the angle range 21 again, the alarm is silenced again. If the marking point M moves back above the inclination tolerance limit 21 before the minimum time has elapsed, however, an alarm is immediately triggered again. In a simple embodiment, the alarm signal may naturally be activated until the minimum time has elapsed.

The alarm apparatus 1 shown comprises a separate power cell 15, such as a battery or a storage battery. Alternatively, power can also be supplied via the connection 14 or it is possible to use the power supply provided in or for the pilot's headset 3.

A radio link, as shown symbolically by the antenna 16, allows a mobile telephone or an onboard radio 17 to be used to output a distress signal if the inclination that is beyond the tolerance continues beyond a predetermined period, which indicates a medical emergency.

The attitude sensor 11 and the unit 110 in the alarm apparatus shown are suitable for mounting on a microphone bow 32 or an earphone 31 of a pilot's headset 3, as shown in FIG. 3.

In this case, the pilot's headset 3 comprises two earphones 31 which are connected by a headband 35 which presses the earphones onto the pilot's ears when they have been put onto the pilot's head. Detection of the mechanical tension in the headband 35 switches on the pilot's headset 3 with the alarm apparatus 1.

If appropriate, the microphone bow 32 may be pivotable, so that it projects in front of the mouth either from the left or from the right side when the pilot's headset is worn. These options mean that the earphone 31 is worn at least over the left or the right ear. The alarm apparatus 1 can be adjusted to suit the respective wearing position by means of a switch 18, as is shown in FIG. 2. Alternatively, the attitude sensor may comprise a position sensor 19 which can be used to automatically determine the respective position. Although the alarm apparatus shown in FIG. 2 has both a switch 18 and a sensor 19, only one of these features is generally necessary.

In one embodiment of the invention, the alarm apparatus 1 is integrated in the electronics of the pilot's headset 3. The attitude sensor 11 is in the form of a micromechanical sensor. In this case, it is likewise possible to have a suitable arrangement with an AMR or GMR sensor or a simple electromechanical sensor which, by way of example, comprises a curved, liquid-filled tube and a matching measurement sensor, for example a Hall sensor or a capacitance sensor. What are known as absolute attitude sensors can also be used in this case.

In order to determine the direction in which the headset 3 is worn, a switch is arranged in or on the hub 50 of the microphone bow 32, so that the measuring device 12 and the computation unit 13 adjust the inclination tolerance limits correctly.

The reference inclination is determined by selecting the position when the pilot's headset 3 is switched on as a reference inclination. In one variation, a calibration momentary-contact switch may also be mounted on the headset 3 which, when operated, sets the instantaneous inclination of the headset 3 as a reference inclination.

In the case of pilots' headsets 3 which have a portion of their electronics in a separate control box situated in the connecting cable, it is naturally also possible for the alarm apparatus 1 to be arranged in appropriately distributed fashion. By way of example, the ear cup 31 may contain only the measuring device 12, and the control box may contain the computation unit 13 with the timer or timers.

In one variation of the invention, the alarm apparatus 1 is arranged essentially outside the pilot's headset 3. In this case, the measuring device 12—which is otherwise of the same design as that described in the preceding paragraphs—is mounted, for example, permanently bonded, on the ear cup 31 of the pilot's headset 3. A cable connection connects the measuring device 12 to the computation unit 13, which in turn is inserted into the connection between the pilot's headset 3 and the aircraft in the manner of an adapter. To this end, the computation unit 13 is arranged in a box which has inputs for connectors on the pilot's headset 3 and outputs, particularly cable connections for the connector, for connection to the aircraft. In this case, the computation unit 13 loops through the signals from the aircraft, particularly the signals from the onboard radio and the intercom, to the pilot's headset 3 and if necessary mixes in the alarm signal. The alarm signal is a multicomponent type. It preferably comprises a voice which speaks aloud a suitable text announcement, for example "Attention, watch airspace", which is also stored with a warning tone, for example a siren tone. In this way, it is a simple matter to avoid confusion given a large number of warning tones in a cockpit of an aircraft. In one simple embodiment, only a text announcement or only a warning tone, that is to say of single-component type, is provided.

The invention claimed is:

1. An alarm apparatus (1) for a pilot's headset (3) which has at least one earphone (31), the alarm apparatus comprising:
   an attitude sensor (11) which detects its inclination relative to a starting position;
   a measuring device (12) for recording a period for which the inclination recorded by the attitude sensor exceeds a stipulated inclination tolerance limit; and
   a computation unit (13) configured to trigger an alarm signal when the recorded period is longer than a preset maximum period;
   wherein the alarm apparatus is configured to be automatically activated when the pilot's headset is put on by a user.

2. The alarm apparatus according to claim 1, wherein the inclination relative to a starting position is a reference inclination or a horizontal inclination.

3. The alarm apparatus according to claim 1, wherein the measuring device (12) is also set up to measure a time for which the inclination recorded by the attitude sensor does not exceed the stipulated inclination tolerance limit, wherein the computation unit (13) for triggering an alarm signal is also set up to terminate a triggered alarm signal only when the inclination tolerance limit is no longer exceeded for a preset minimum period of time as a minimum time.

4. The alarm apparatus according to claim 1, wherein the measuring device (12) is also set up to measure a time for which the inclination recorded by the attitude sensor does not exceed the stipulated inclination tolerance limit, wherein the computation unit (13) for triggering an alarm signal is also set up to terminate a triggered alarm signal immediately when the inclination tolerance limit is no longer exceeded, but is triggered again immediately when the stipulated inclination tolerance limit is exceeded again before a minimum period of time has elapsed.

5. The alarm apparatus according to claim 1, wherein the computation unit (13) for triggering an alarm signal is also set up to intensify a triggered alarm signal over time.

6. The alarm apparatus according to claim 1, wherein the alarm signal is an audible warning signal.

7. The alarm apparatus according to claim 1, wherein the alarm signal is a visual warning signal.

8. The alarm apparatus according to claim 1, wherein the preset maximum period is between 2 and 60 seconds.

9. The alarm apparatus according to claim 8, wherein the preset maximum period is less than 40 seconds.

10. The alarm apparatus according to claim 8, wherein the preset maximum period is less than 20 seconds.

11. The alarm apparatus according to claim 1, wherein the preset maximum can be changed or stipulated by a user.

12. The alarm apparatus according to claim 1, wherein the inclination tolerance limit is at least one of ±5°, ±10°, ±15°, ±20° around the starting position.

13. The alarm apparatus according to claim 1, wherein the inclination tolerance limit can be adjusted by a user.

14. The alarm apparatus according to claim 1, wherein the inclination tolerance limit is provided asymmetrically.

15. The alarm apparatus according to claim 1, wherein the alarm apparatus is powered by a battery (15) or a storage battery that is provided separately for the alarm apparatus or a connector (14) for connection to a power supply for the pilot's headset (3).

16. A pilot's headset (3) having at least one earphone (31), the pilot's headset having an alarm apparatus (1) according to claim 1.

17. The pilot's headset according to claim 16, wherein the alarm signal is an audible warning signal which is output via the at least one earphone (31) of the pilot's headset (3).

18. A method for controlling an alarm apparatus (1) for a pilot's headset (3), according to claim 1, comprising the following steps:
   recording the exceeding of a limit value for an inclination of the pilot's headset;
   establishing that the exceeding of the limit value for the head inclination exceeds a preset period; and
   outputting an audible warning signal via at least one earphone (31) of the pilot's headset (3).

19. An alarm apparatus (1) for a pilot's headset (3) which has at least one earphone (31), the alarm apparatus comprising:
   an attitude sensor (11) which detects its inclination relative to a starting position;
   a measuring device (12) for recording a period for which the inclination recorded by the attitude sensor exceeds a stipulated inclination tolerance limit;
   a computation unit (13) configured to trigger an alarm signal when the recorded period is longer than a preset maximum period, and
   a microphone bow (32) on or in which the alarm apparatus (1) is mounted, wherein the microphone bow (32) is able to pivot and can be held either in a left or in a right wearing position, wherein the alarm apparatus (1) is adjustable by a switch (18) or a position sensor (19) to suit the microphone bow (32) being held in the left or in the right wearing position.

20. An alarm apparatus (1) for a pilot's headset (3) which has at least one earphone (31), the alarm apparatus comprising:
   an attitude sensor (11) which detects its inclination relative to a starting position;
   a measuring device (12) for recording a period for which the inclination recorded by the attitude sensor exceeds a stipulated inclination tolerance limit; and
   a computation unit (13) configured to trigger an alarm signal when the recorded period is longer than a preset maximum period;
   wherein the measuring device (12) is also set up to measure a time for which the inclination recorded by the attitude sensor does not exceed the stipulated inclination tolerance limit, wherein the computation unit (13) for triggering an alarm signal is also set up to terminate a triggered alarm signal only when the inclination tolerance limit is no longer exceeded for a preset minimum period of time as a minimum time.

21. An alarm apparatus (1) for a pilot's headset (3) which has at least one earphone (31), the alarm apparatus comprising:
   an attitude sensor (11) which detects its inclination relative to a starting position;
   a measuring device (12) for recording a period for which the inclination recorded by the attitude sensor exceeds a stipulated inclination tolerance limit; and
   a computation unit (13) configured to trigger an alarm signal when the recorded period is longer than a preset maximum period;

wherein the measuring device (12) is also set up to measure a time for which the inclination recorded by the attitude sensor does not exceed the stipulated inclination tolerance limit, wherein the computation unit (13) for triggering an alarm signal is also set up to terminate a triggered alarm signal immediately when the inclination tolerance limit is no longer exceeded, but is triggered again immediately when the stipulated inclination tolerance limit is exceeded again before a minimum period of time has elapsed.

\* \* \* \* \*